(12) United States Patent
Yundt

(10) Patent No.: US 7,166,110 B2
(45) Date of Patent: Jan. 23, 2007

(54) METHOD, SYSTEM AND APPARATUS FOR INTERBODY FUSION

(76) Inventor: Kent D. Yundt, 1791 NW. Remarkable Dr., Bend, OR (US) 97701

( * ) Notice: Subject to any disclaimer, the term of this patent is extended or adjusted under 35 U.S.C. 154(b) by 0 days.

(21) Appl. No.: 11/031,511

(22) Filed: Jan. 7, 2005

(65) Prior Publication Data

US 2005/0154460 A1   Jul. 14, 2005

Related U.S. Application Data

(60) Provisional application No. 60/535,227, filed on Jan. 9, 2004.

(51) Int. Cl.
*A61B 17/56* (2006.01)
*A61F 2/44* (2006.01)

(52) U.S. Cl. .................... 606/61; 623/17.11
(58) Field of Classification Search .......... 606/61, 606/99, 90, 60, 192; 623/17.11, 17.16
See application file for complete search history.

(56) References Cited

U.S. PATENT DOCUMENTS

| | | | |
|---|---|---|---|
| 3,486,505 A * | 12/1969 | Morrison | 606/90 |
| 4,045,418 A | 8/1977 | Sinclair | |
| 5,431,658 A * | 7/1995 | Moskovich | 606/99 |
| 5,549,679 A | 8/1996 | Kuslich | |
| 6,039,761 A * | 3/2000 | Li et al. | 623/17.16 |
| 6,425,920 B1 * | 7/2002 | Hamada | 623/17.16 |
| 6,488,710 B1 * | 12/2002 | Besselink | 623/17.15 |
| 6,582,431 B1 | 6/2003 | Ray | |
| 6,652,533 B1 * | 11/2003 | O'Neil | 606/100 |
| 6,740,093 B1 | 5/2004 | Hochschuler et al. | |
| 6,755,841 B1 * | 6/2004 | Fraser et al. | 606/99 |

OTHER PUBLICATIONS

Sep. 1999, Ullrich PF: Lumbar Disc Herniation, www.spine-health.com.
Sep. 1999, Ullrich PF: Posterior Lumbar Interbody Fusion (PLIF), www.spine-health.com.
Sep. 1999, Ullrich PF: Anterior Lumbar Interbody Fusion (ALIF), www.spine-health.com.
Sep. 1999, Ullrich PF: Pedicle Screws, www.spine-health.com.
Sep. 1999, Ullrich PF: Anterior Interbody Cages, www.spine-heatlh.com.
Sep. 1999, Ullrich PF: Back Surgery and Neck Surgery, www.spine-health.com.
May 2002, Regan JJ: Spondylosis (Spinal Osteoarthritis), www.spineuniverse.com.
Jun. 2002, Salerni AA: A Minimally Invasive Approach for Posterior Lumbar Interbody Fusion, *Neurosurgical Focus* 13(6), 2002.
Mar. 2004, Robbins MM, Vaccaro AR, Madigan L: The Use of Bioabsorbable Implants in Spine Surgery, *Neurosurgical Focus* 16(3), 2004.
Mar. 2004, Kuklo TR, Rosner MK, Polly DW: Computerized Tomography Evaluation of a Resorbable Implant After Transforminal Lumbar Interbody Fusion, *Neurosurgical Focus* 16(3), 2004.

* cited by examiner

*Primary Examiner*—Pedro Philogene
(74) *Attorney, Agent, or Firm*—Alleman Hall McCoy Russell & Tuttle LLP

(57) ABSTRACT

Methods, systems and apparatus are provided for interbody fusion. In some embodiments, a device is provided for fusing vertebral bodies. The device includes a shell configured to be disposed between a first body and a second body, an injection opening to receive fusing material, and a delivery hole configured to enable fusing material to flow into at least one of the first body and the second body.

11 Claims, 10 Drawing Sheets

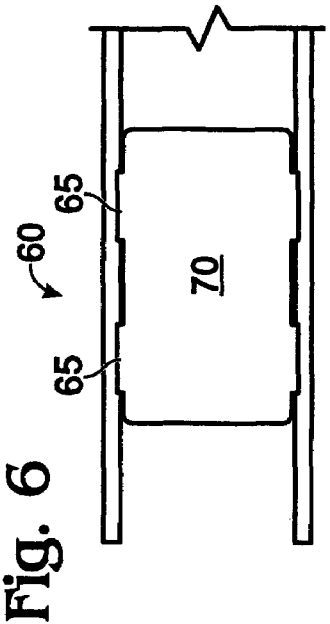
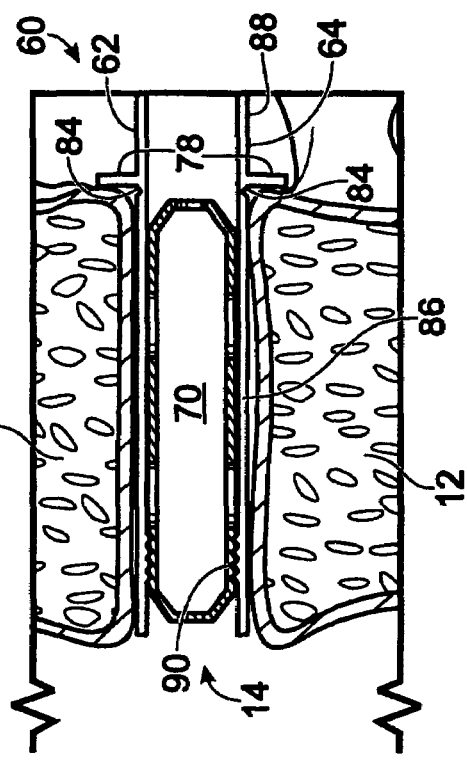
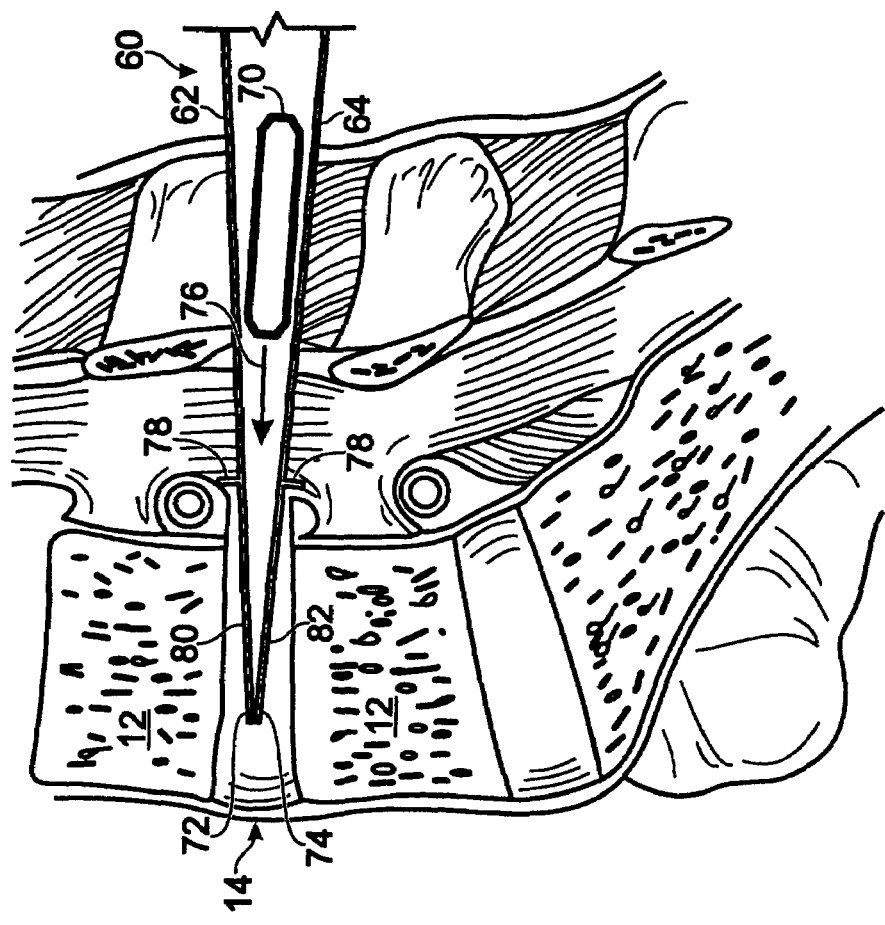

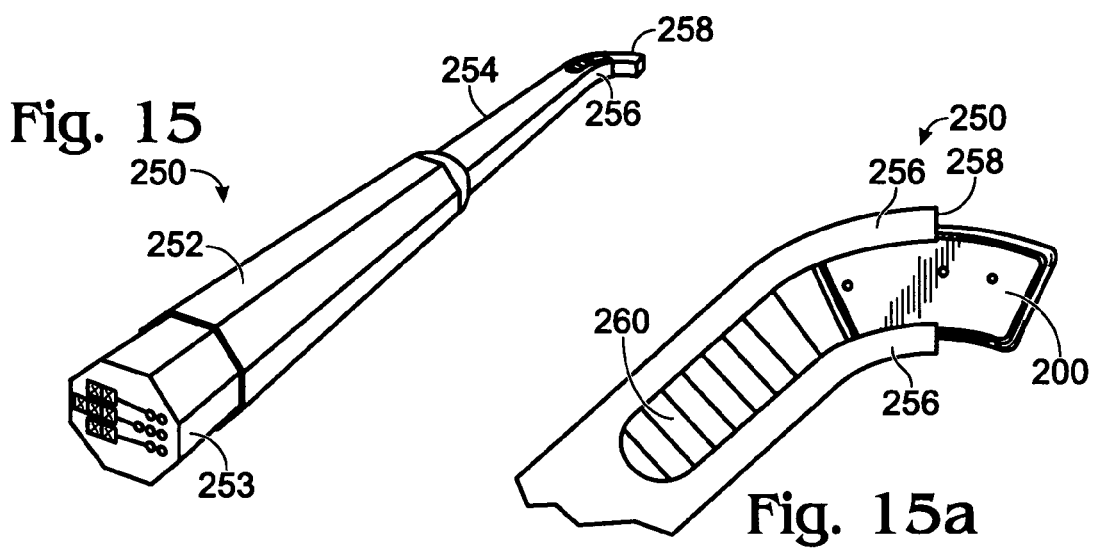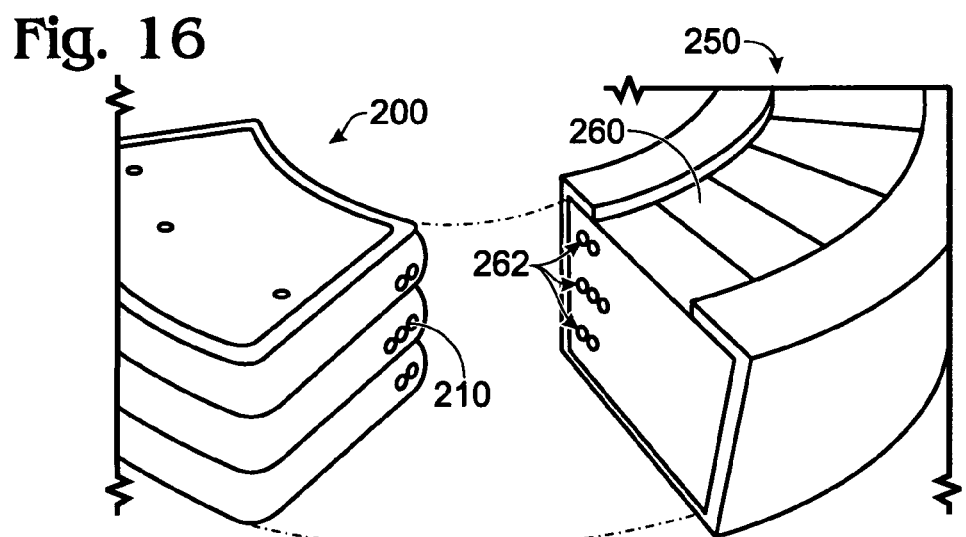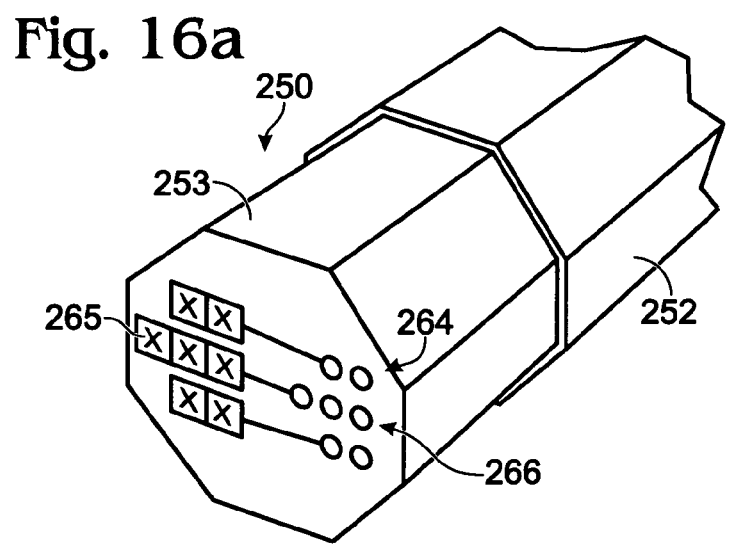

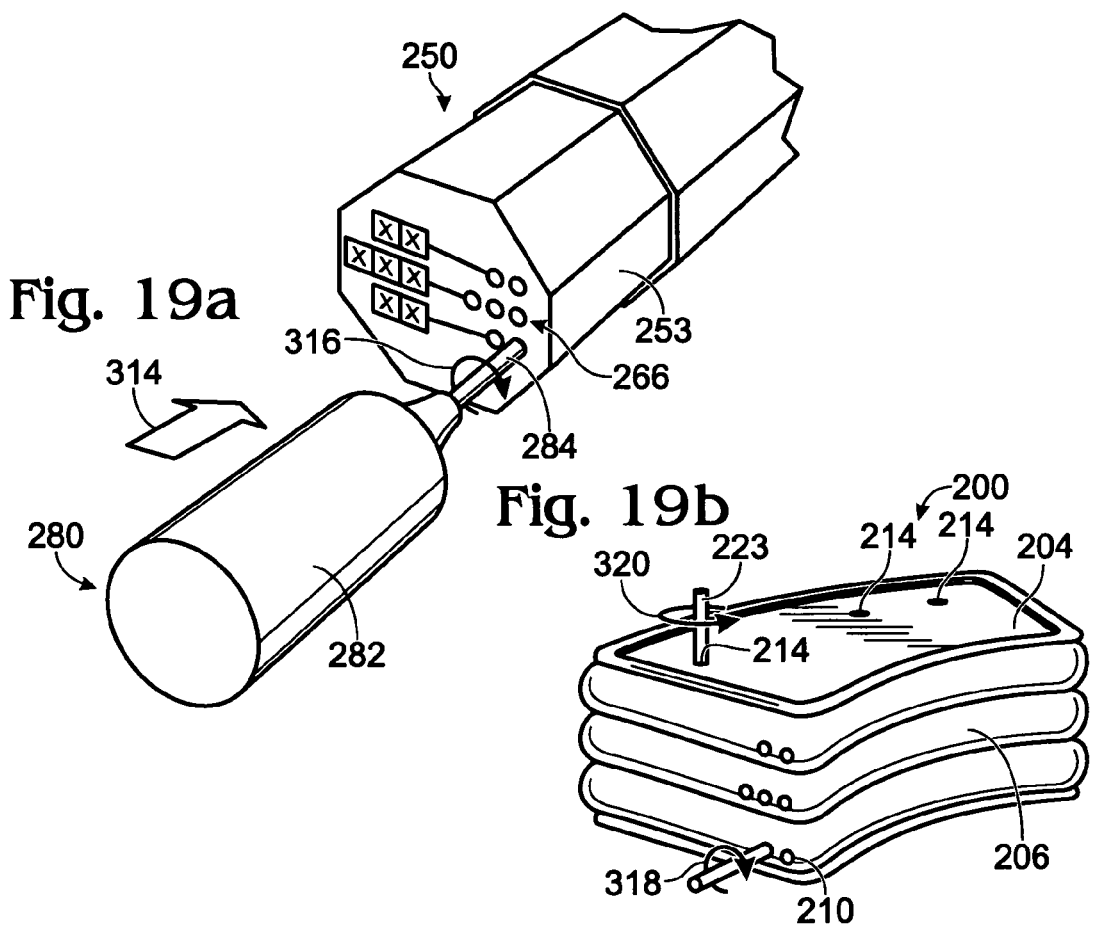
Fig. 19a
Fig. 19b
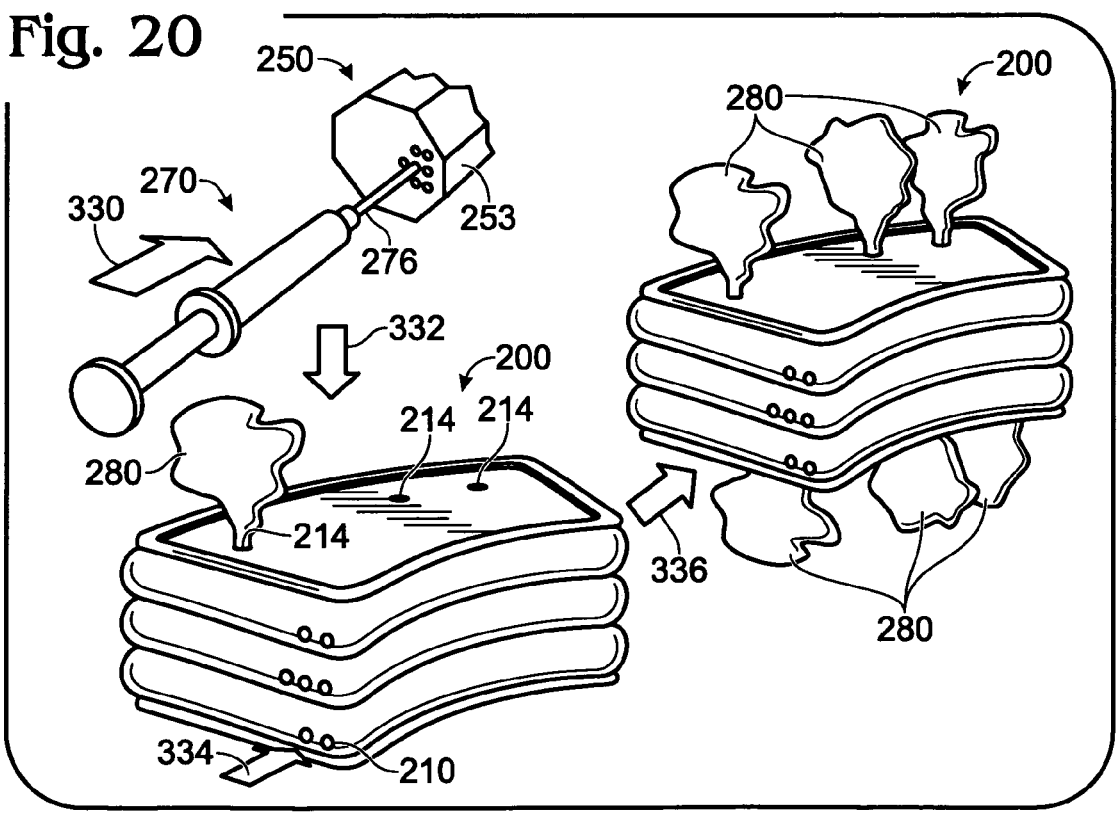
Fig. 20

METHOD, SYSTEM AND APPARATUS FOR INTERBODY FUSION

CROSS-REFERENCE TO RELATED APPLICATIONS

The present U.S. patent application claims the benefit of U.S. Provisional Patent Application Ser. No. 60/535,227 filed Jan. 9, 2004, the entire contents of which are hereby incorporated herein by reference in their entirety for all purposes.

FIELD

The present disclosure relates generally to methods, systems, and apparatus for interbody fusion, and more particularly, to methods, systems, and apparatus for interbody fusion of one or more adjacent vertebral bodies.

BACKGROUND

Back and neck pain may cause disability and discomfort which may affect an individual's lifestyle. There are various levels of back and neck pain, from a low-level annoyance to extreme discomfort and debilitating pain. Depending on the type of pain and the cause of the pain, multiple options may be available to reduce and/or treat back and neck pain. Where conservative non-invasive techniques are inadequate, surgical treatment options may be available to reduce or eliminate such back and/or neck pain. For example, surgical treatment options may be used to decompress a nerve root, stabilize a lumbar or cervical joint, reduce a deformity of the spine, etc.

The degeneration, rupture or herniation of the intervertebral discs of the spine may cause back or neck pain. One exemplary type of lower back pain is due to degeneration of lumbar discs in the spine. Surgical options, such as lumbar fusion, may be available to relieve such lower back pain.

Two common types of lumbar fusion are postlateral fusion (PLF) and interbody fusion, including anterior lumbar interbody fusion (ALIF) and posterior lumbar interbody fusion (PLIF). In the lumbar fusion methods, described briefly below, a metal construct is often used to temporally stabilize the motion segment while awaiting development of a rigid osseous construct.

PLF may include positioning a bone graft external to the ruptured disc such that adjacent spinal bones (spinal segments) grow together. Screws and plates, such as pedicle screws, may be used to stabilize and prevent motion of adjacent spinal bones as they fuse together. Because PLF is not an interbody fusion, the surgery may be easier. However, PLF may not relieve back pain in some situations because the damaged disc remains intact within the spine and may continue to cause discomfort.

Each of the interbody fusions includes inserting a bone graft or similar object directly into the disc space. ALIF is an interbody fusion where the incision is through the front side of the body, such as through the abdomen. Typically, a three to five inch incision may be made on the abdomen. Through this incision, one or more lumbar discs may be removed. The discs may be replaced with a bone graft and/or a fusion cage. Because the large blood vessels to the lower extremities lay on top of the spine, the skill of a vascular surgeon may be needed to gain access to the spine. Moreover, there may be an increase in the risk of complications, such as hemorrhage, due to the close proximity of the large blood vessels to the spine. The risk of other complications, including unintentional sympathectomy and retrograde ejaculation in males, may also increase.

PLIF is an interbody fusion where entry is through the backside of the body. Typically, a three to six inch long incision in the midline of the back may be cut to obtain access to the spine. Due to the backside entry, substantial retraction of the nerve roots is necessary to gain access to the disc space. PLIF may further require extensive bone removal to access the disc space, which may increase the possibility of posterior migration of a fusion cage. Furthermore, the backside entry often damages the muscle tissue surrounding the disc space and adjacent spinal bones. The damage to the surrounding muscles complicates and prolongs the recovery process. Additionally, there may be an increased risk in extensive blood loss due to the epidural veins over the disc space.

For both ALIF and PLIF, the quality of the adjacent spinal bones may affect the quality and success of the fusion. For example, conditions characterized with poor bone quality, such as osteopenia and osteoporosis, may significantly decrease fusion rates. As described above, the conventional fusion methods may result in complications, such as neurological, dural, osteal, and muscular complications. Moreover, in many situations, these procedures require long hospital stays.

SUMMARY

Methods, systems and apparatus are provided for interbody fusion. In some embodiments, a device is provided for fusing vertebral bodies. The device may include a shell configured to be disposed between a first body and a second body, an injection opening to receive fusing material, and a delivery hole configured to enable fusing material to flow into at least one of the first body and the second body.

BRIEF DESCRIPTION OF THE DRAWINGS

FIG. 5 is a simplified side view of an alternative embodiment of the delivery device being disposed in a disc space with a material restrictor being funneled into the disc space according to an alternative embodiment of the present disclosure.

FIG. 6 is a schematic illustration of a delivery device and a material restrictor according to an embodiment of the present disclosure.

FIG. 7 is a side view of a delivery device and a material restrictor disposed in a disc space.

FIGS. 15 and 15a are schematic illustrations of a delivery device according to an embodiment of the present disclosure.

FIGS. 16 and 16a are further illustrations of the delivery device of FIGS. 15 and 15a and a material restrictor showing operative attachment of the delivery device to the material restrictor according to an embodiment of the present disclosure.

FIGS. 19a and 19b illustrate drilling of delivery channels into adjacent vertebral bodies according to an embodiment of the present disclosure.

FIG. 20 illustrates delivery of fusing material into adjacent vertebral bodies according to an embodiment of the present disclosure.

DETAILED DESCRIPTION

Figure 1:
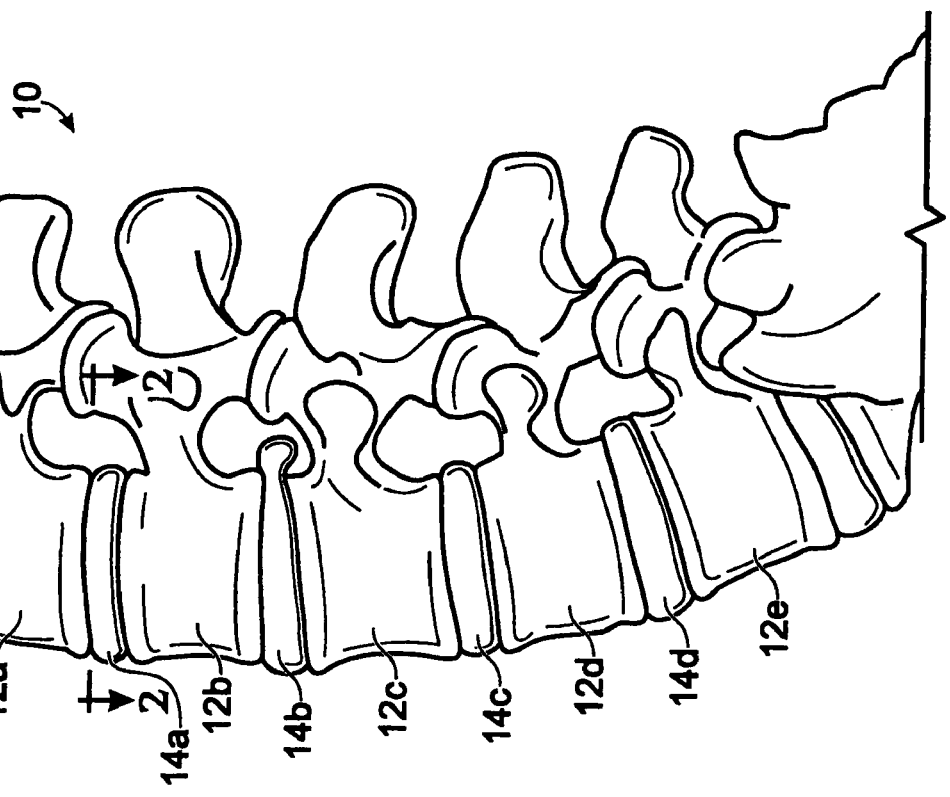
FIG. 1 is a simplified lateral view of the lumbar region of the spinal column.

FIG. 1 illustrates generally a simplified lateral view of the lumbar region of the spinal column 10. Spinal column 10 includes a plurality of separate bones or vertebral bodies 12a–12e. Interposed the vertebral bodies 12 are intervertebral discs 14a–14d. The intervertebral discs may function as both ligaments and as shock absorbers. Damage to, or rupture of, these discs may be treated by fusing two or more of the vertebrae together.

Although the present disclosure describes fusing one or more vertebral bodies in the lumbar region, it should be appreciated that similar methods, systems, and apparatus/devices may be used to fuse bones of other regions of the spinal cord or elsewhere in the body. For example, the methods, systems, and/or apparatus may be used to fuse the cervical region of the spine, the thoracic region of the spine, or other regions of the body with adjacent bones that may be fused together. Moreover, such disclosure is described in regards to fusing human bones together, however, it is possible that the disclosed methods, systems, and apparatus may be used in veterinary practice.

Figure 2:
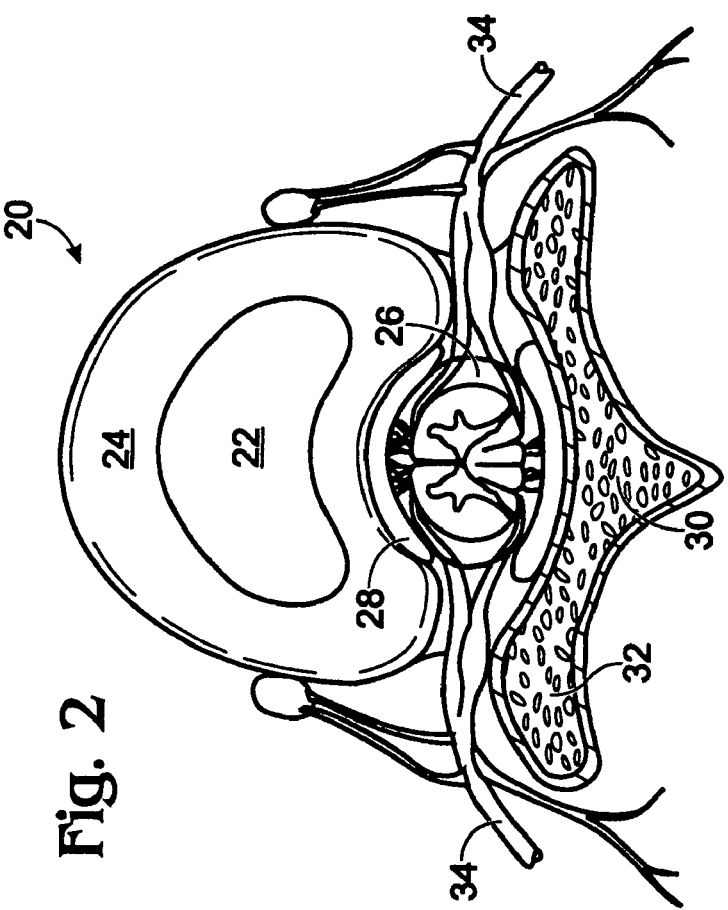
FIG. 2 is a simplified axial view of a lumbar vertebral body and a disc.

For ease of reference and to better understand the present disclosure, FIG. 2 illustrates schematically, at 20, an axial view of a typical intervertebral disc. Disc 20 includes a nucleus pulposus 22, which is a gel-like region in the center of the disc. Nucleus pulposus 22 is surrounded by the annulus fibrosus 24. Attached to the outer portion of annulus fibrosus 24, adjacent thecal sac 26, is posterior longitudinal ligament (PLL) 28. Thecal sac 26 is disposed between PLL 28 and lamina 30 and facets 32 of the spine. Thecal sac 28 may be an entry point for spinal nerves 34 and may wrap or surround other neural material.

Figure 3:
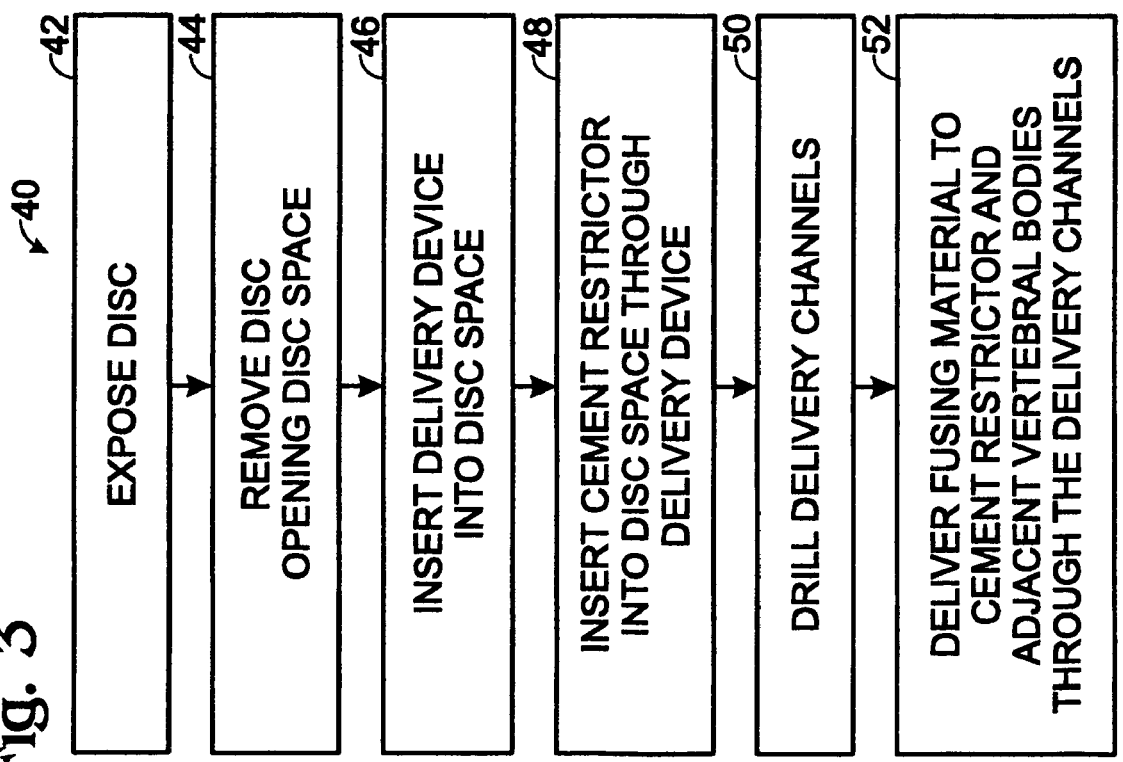
FIG. 3 is a block diagram of a method for augmented micro lumbar interbody fusion (AMLIF) according to an embodiment of the present disclosure.

In one embodiment of the present disclosure, as shown in block diagram format in FIG. 3, a minimally-invasive method 40 (referred to herein as augmented micro lumbar interbody fusion (AMLIF)) is provided for fusing two or more vertebral bodies. Method 40 is a minimally-invasive method that addresses the difficulties surrounding current fusion techniques, such as PLF, PLIF, ALIF. AMLIF may simplify lumbar fusions by providing a minimally invasive approach that may decrease morbidity and the length of post-operative hospital stays, while keeping the arthrodesis rate high. For example, in some embodiments, the AMLIF may be so minimally invasive to allow for same day surgery.

Moreover, the AMLIF procedure may expand patient selection criteria. For example, the AMLIF procedure may be used on soft poor quality bone (as seen with osteoporosis), thus providing additional options for such patients. In some embodiments, AMLIF further may be used with patients with lumbar disc herniation, and other like conditions, to decrease the risk of recurrent disc herniation and progressive degenerative spondylosis.

Additionally, the AMLIF procedure may be practiced by spine surgeons, using known skills, without requiring additional specialization. Thus, most neurosurgeons and orthopedic spine surgeons will be able to use the AMLIF technique with low risk.

As described in more detail below, AMLIF further may provide a method for distraction to aid in foraminal decompression, reestablishing disc space height and maintaining normal lordotic curvature. In some embodiments, the AMLIF method and the associated hardware may function to reduce and/or avoid subsidence, hardware migration, and hardware failure, thus, providing solid long-term segmental fusion.

Referring specifically to FIG. 3, AMLIF may include exposure of a disc, as indicated at 42. Several different methods may be used to expose the disc. Typically, such methods may include making an incision through the epidermis and the dermis followed by incising, retracting, or removing muscles, nerves, and bones to reveal the disc in the intervertebral space.

For example, exposure of the disc, at 42, may be achieved through a small incision. The incision may be a small 2–3 cm midline incision. The incision may be smaller or larger, such as between about 0.5 cm and about 5 cm, for endoscopic placement or when more than one disc is to be removed. This small incision is in contrast to conventional posterolateral fusions that typically require large incisions, on the order of three to six inches.

The small midline incision of the present disclosure also may be used for endoscopic placement. Similar to the small midline incision through the epidermis and the dermis, a small incision, e.g. less than approximately 5 cm, may be made through muscle tissue that may be disposed between the disc space and the initial incision. The petite incision may help to preserve posterior stabilizing structures.

Following incision, and similar to a micro lumbar discectomy, bilateral partial hemilaminotomies may be completed to expose the disc space. Additionally, neural material, such as the thecal sac and nerve roots, may require gentle retraction to provide access to the exposed disc space. The neural material may also be retracted during other steps of the method to provide access to the disc space. Although the disc is exposed for the purpose of interbody fusion, other pathology, such as herniated disc material, lateral recess stenosis, spinal stenosis, etc., may be dealt with as desired once the disc is exposed.

Following exposure of the disc, the posterior longitudinal ligament and annulus may be incised and the disc may be removed (as indicated at 44). It should be understood that it may not be desirable or necessary to remove the entire disc, but that at least a portion of the disc material may be removed to open a disc space. Removal of the disc material may be accomplished using any suitable method to open the disc space.

After removal of the disc, a delivery device may be inserted into the disc space, at 46. The delivery device (described in more detail below) may be adapted to deliver a material restrictor or cage (referred to also as a fusion restrictor and described in more detail below) into the disc space. In some embodiments, the delivery device may include structure to enable insertion of the material restrictor. In other embodiments, the delivery device may include a selectively detachable portion which may function as the material restrictor. Moreover, in some embodiments, the delivery device may have multiple purposes, including aiding in opening the disc space, aiding in drilling delivery channels, and or aiding in delivering fusing material into the material restrictor. The delivery device and the size of the material restrictor may simplify the fusion procedure and may be a minimally-invasive tissue destruction approach.

As briefly described above, a material restrictor or interbody space or stabilizer may be selectively positioned in the disc space, as indicated at 48 in FIG. 3. For example, in some embodiments, during or following positioning of delivery device 60, the material restrictor or cement restrictor may be inserted into the disc space using delivery device 60, at 48. In one embodiment of the method, material restrictor 70 is impacted down (tapped down) through delivery device 60 from the proximal end of the delivery device to the distal end of the delivery device.

Delivery device may include a guide configured to be at least partially disposed in the disc space and configured to funnel or guide the material restrictor into a select position within the disc space. The guide may be any suitable device. For example, in one embodiment, the guide may include projections or tangs adapted to be at least partially positioned within the disc space. The projections or tangs may be elongated slides which enable positioning of a restrictor into the disc space. As described in more detail below, the tangs may include alignment features which may be used to guide positioning of the restrictor into the disc space. A portion of the tangs may be sized to correspond to the opened disc space.

As the restrictor is impacted through the delivery device, in some embodiments, the force may separate the tangs (or similar structure) of the delivery device distracting the disc space. Thus, impacting the restrictor into the disc space may function to reestablish normal anatomic disc space and decompress the adjacent neural foramina. The delivery device may be guided into position by structures or features on the delivery device, on the material restrictor, or on both the delivery device and the material restrictor.

As briefly described above, the delivery device may function as a retractor to temporarily retract neural material such as a nerve root and/or a thecal sac. Additionally, the delivery device may be configured to act as a distractor to spread adjacent vertebral bodies that may be at least partially collapsed after removal of the disc material. In some embodiments, the delivery device may be configured with a proximal end operable by a practitioner, such as a physician or surgeon performing the procedure and with a distal end configured to be disposed in the disc space. The practitioner may use the delivery device to open the disc space to a select size to accommodate the material restrictor and reestablish normal anatomic disc space height.

The material restrictor may be inserted through the delivery device until it reaches a predetermined or select position within the delivery device. For example, in some embodiments, the select position in the delivery device to which the material restrictor is inserted may be disposed adjacent the distal end of the delivery device. In one embodiment, the restrictor may be positioned substantially intermediate the adjacent vertebral bodies.

As described in more detail below, the delivery device may include one or more structures to aid in insertion, removal and placement of the delivery device. For example, the delivery device may be configured with one or more stops configured to rest against the posterior surfaces of the vertebral bodies when the delivery device is fully inserted.

Figure 4:
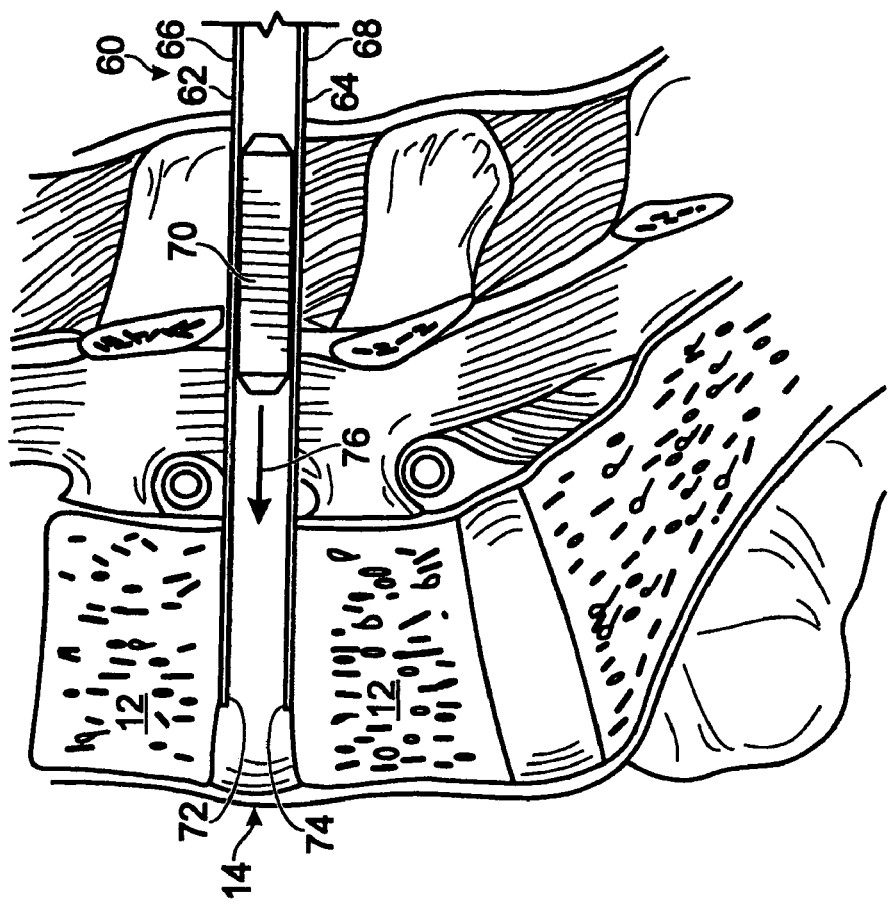
FIG. 4 is a simplified side view of a delivery device disposed in a disc space with a material restrictor being funneled into the disc space according to an embodiment of the present disclosure.

Although any suitable delivery device may be used in the method of the present disclosure, one exemplary delivery device 60 includes two delivery tangs configured to be positioned into the disc space as shown in FIG. 4. As can be seen in the figure, first and second elongate tangs 62, 64 may include cooperating first and second proximal ends 66, 68, respectively, configured to receive a material restrictor 70. First and second elongate tangs 62, 64 also may include cooperating first and second distal ends 72, 74 configured to be at least partially inserted into disc space 14. As described above, disc space 14 may be at least partially collapsed due to the removal of the disc material in the prior step. The delivery device 60 may be configured to allow the material restrictor 70 to be inserted from the proximal ends 66, 68 to a predetermined position adjacent the distal ends 72, 74. In other words, tangs 62, 64 may be configured to be spaced apart relative to each other to enable placement of a material restrictor 70.

Insertion of delivery device 60 into the disc space may be accomplished in. any suitable fashion. For example, tangs 62, 64 may be shaped to enable insertion into the disc space. For example, in FIG. 5, tangs 62 and 64 are angled together forming a tip which may be initially pushed into the disc space. The tangs may be separated to form a channel for insertion of the restrictor. In other embodiments, tangs 62, 64 may be shaped or curved to accommodate insertion. The tangs may be separated as the restrictor is driven through the tangs into the space.

As shown in FIG. 5, tangs 62, 64 may include projections and other structures that are configured to stabilize and position delivery device 60 and/or restrictor 70. For example, tangs 62, 64 may include stops 78 spaced from distal ends 72, 74 of the tangs. As tangs 62, 64 are positioned within the disc space, stops 78 may flex or otherwise slide or pass along the opening or channel towards the disc space. Stops 78 may be configured to rest against the posterior surfaces of the vertebral bodies adjacent disc space 14 (as shown in FIG. 7) such that portions 80 and 82 are substantially disposed within the disc space. Regardless of the configuration, stops 78 or other similar structures, may be configured to enable proper positioning of tangs 62, 64 relative the disc space so as to enable proper positioning of material restrictor 70 in the disc space.

In some embodiments, stops 78 may limit anterior migration of tangs 62, 64 as delivery device 60 is inserted into disc space 14. Stops 78 also may be configured to limit anterior migration of delivery device 60 during remaining steps of the method discussed in FIG. 3. In some embodiments, stops 78 may be disposed at a length from distal ends 72, 74 ranging from about 20 mm to about 26 mm. However, other positions are possible and are within the scope of the disclosure. Moreover, there may be additional stops or structures which cooperate to position tangs 62, 64. Moreover, in some embodiments, the end of the tangs or other portion of the tangs may protect the restrictor and/or guide placement of the restrictor. It should be recognized that the distance to which stops 78 are spaced from distal ends 72, 74 may be determined by considering such factors as the size of vertebral bodies being fused, the size of material restrictor 70 to be inserted, and the desired position of material restrictor 70 between the vertebral bodies, such as vertebral bodies 12.

Delivery device 60 also may be configured to retract the neural material adjacent the disc space 14 to further protect the neural material during the procedure. In some embodiments, delivery device 60 may include a retractor component configured to temporarily displace neural material. For example, delivery device 60 may include a medial slightly curved tang or tangs (not shown) that may function as a nerve root retractor.

With reference to FIG. 5, delivery device 60 may be configured to enable the insertion of a material restrictor into a collapsed disc space and to reestablish normal disc space height without damaging the endplates. A typical bilateral partial hemilaminotomy used to provide access to disc space 14 may be used to provide an opening that is on average about 7 mm wide. Unlike the present system which requires only a small opening, conventional systems, such as ALIF or PLIF systems may be difficult to use since such systems require a larger opening then the 7 mm of width (or other small region) provided for the AMLIF system. Also, unlike other systems, the present system does not have pedicle screws against which to distract.

Further, unlike some PLIF systems that function by placing a relatively narrow cage into the disc space in a horizontal position and then rotating the cage into a vertical position, thus distracting the disc space, the present system does not provide enough space for such rotation. Specifically, a 12 mm cage placed horizontal into a disc space requires an opening at least 12 mm wide, which is substantially more than the 7 mm space created through the method of the present disclosure.

In one embodiment according to the present disclosure, delivery device 60 may be configured to distract disc space 76. Delivery device 60 may be configured with first and second tangs 62, 64, as described above, and disc space 14 may be distracted as material restrictor 70 is inserted through the delivery device into the predetermined position. As can be seen in FIG. 5, first and second distal ends 72, 74 may be configured to be initially substantially adjacent to one another as delivery device 60 is inserted into disc space 76 (as indicated by arrow 76). Insertion and impaction of material restrictor 70 into delivery device 60 may operate to spread first and second distal ends 72, 74 apart to accommodate the material restrictor. Impaction of the restrictor down through the delivery device may function to reestablish normal anatomic disc height and decompress the adjacent neural foramina.

In some embodiments, delivery device 60 may be provided with a coupling (not shown) extending between the first and second tangs 62, 64. The coupling may be configured to couple tangs 62, 64 while not interfering with the insertion of material restrictor 70. In some embodiments, material restrictor 70 may act as a fulcrum as it is inserted through delivery device 60 providing a pivot point about which the tangs may be rotated to distract the disc space 76 as described above. The coupling may be configured to assist in the distraction of the disc space by providing a fixed point about which the elongate tangs can rotate as distal ends 72, 74 are spread apart and proximal ends 66, 68 are brought together. Additionally, the coupling may be configured to allow rotation through only a limited range to prevent over-rotation of tangs 62, 64.

It should be appreciated that other types of couplings, or no coupling, may be provided or necessary depending on the configuration of the delivery device. Moreover, the coupling may be releasable such that the restrictor is able to break through the coupling to a select position. In some embodiments, the coupling may operate to lock or secure the restrictor in a select position.

FIG. 6 provides another schematic illustration of a material restrictor 70 being inserted through delivery device 60. As discussed in more detail below, the material restrictor and the tangs may have corresponding or mating structure 65, such as a channel and groove system, which aids in alignment and positioning of the material restrictor during insertion.

FIG. 7 illustrates some of the additional features that may be incorporated into embodiments of delivery device 60. Other features and structures may be incorporated into delivery device 60 as appropriate for use in different surgical applications. Exemplary features that may be incorporated when the delivery device 60 is used for interbody fusion of adjacent vertebral bodies include frangible joints, positioning structures, and alignment structures.

Exemplary frangible joints 84 intermediate the distal ends and the proximal ends of tangs 62, 64 are shown in FIG. 7 adjacent stops 78. Frangible joints 84 may be configured to couple a restrictor portion 86 of each tang to a handle portion 88 of each tang. Restrictor portion 86 may be configured to extend into the disc space. In some embodiments, restrictor portion 86 may be adapted to remain within disc space 76, while handle portion 88 may be adapted to be removed from the patient at some point during the operation. In other words, restrictor portion 86 may be removable from handle portion 88.

It should be appreciated that frangible joints 84 may be disposed at any point along the length of the tangs 62, 64. As shown in FIG. 7, for example, frangible joints 84 may be disposed distally from stops 78 allowing the stops to be removed as part of handle portion 88. However, other locations for frangible joints 84 are within the scope of the present disclosure.

In some embodiments, frangible joints 84 or deliver device 60 may be coated with a sealing material. Any suitable sealing material may be used. The coating may be used to aid in positioning the device, preventing leakage or degradation of the material composing the joints or delivery device, or any other suitable purpose.

FIG. 7 also illustrates exemplary positioning features or structures 90 of delivery device 60. Positioning features 90 may be configured to ensure accurate positioning and stabilization of restrictor 70. Any suitable positioning structures may be provided, including, but not limited to projections, ridges, teeth, detents, receiving openings, channels, locking buttons, etc.

Positioning features 90 may cooperate with material restrictor 70 to provide feedback to the user when the material restrictor is disposed in the desired predetermined position. Further, such positioning features may be configured to aid in retention of the material restrictor in the predetermined position. A variety of structures may be utilized as positioning features 90 to provide the feedback and/or retention. One example is shown in FIG. 7 where the delivery device 60 includes a toothed ridge on the inside surface of at least one of the tangs 62. The ridge may be configured to mate with a groove, teeth, etc. disposed on the exterior surface of the material restrictor 70 (described in more detail below). Although shown as having corresponding structure on the restrictor, it should be noted that the tangs may include structure which does not require any corresponding structure on the restrictor. For example, the tangs may include a raised bump which upon pressure by the restrictor (regardless of surface structure) is depressed, thus applying a retainment force against the restrictor.

In other embodiments, positioning features 90 may be provided with a groove on at least one of the tangs configured to mate or correspond with a ridge disposed on the material restrictor. Other structures and arrangements may be used to secure the restrictor and/or provide feedback to the user. The feedback provided to the user may be audible, visible, or tactile feedback. For example, a click may be heard when material restrictor 70 reaches a desired predetermined position. Alternatively, the amount of force required to further insert material restrictor 70 may increase upon reaching the predetermined position. Other forms of feedback are available and are within the scope of the present disclosure.

Additionally and/or alternatively, delivery device 60 may include alignment features, such as channels and grooves, configured to cooperate with material restrictor 70 to guide the material restrictor through delivery device 60 during insertion of the material restrictor. A variety of structures may be utilized to retain the material restrictor within the delivery device 60. For example, each of the tangs 62, 64 may include a lip at the outer side edges (not shown). Alternatively, one or more of the tangs and/or material restrictor may be provided with longitudinal projections, ridges, grooves, channels, depressions, bumps, etc. configured to aid in alignment of the restrictor. In some embodiments, mating structures may be provided on one or more of the tangs and/or on material restrictor 70.

As discussed above in connection with delivery device 60, the step of inserting material restrictor 70 into disc space 14 may distract the disc space. The extent to which the disc space is distracted may be dependent on the dimensions of the material restrictor. It should be understood that the dimensions and configuration of material restrictor 70 may be selected to reestablish normal anatomic disc space and to decompress the adjacent neural foramina. Other dimensions and configurations may be selected according to the practitioner's preference and patient's needs.

Figure 8:
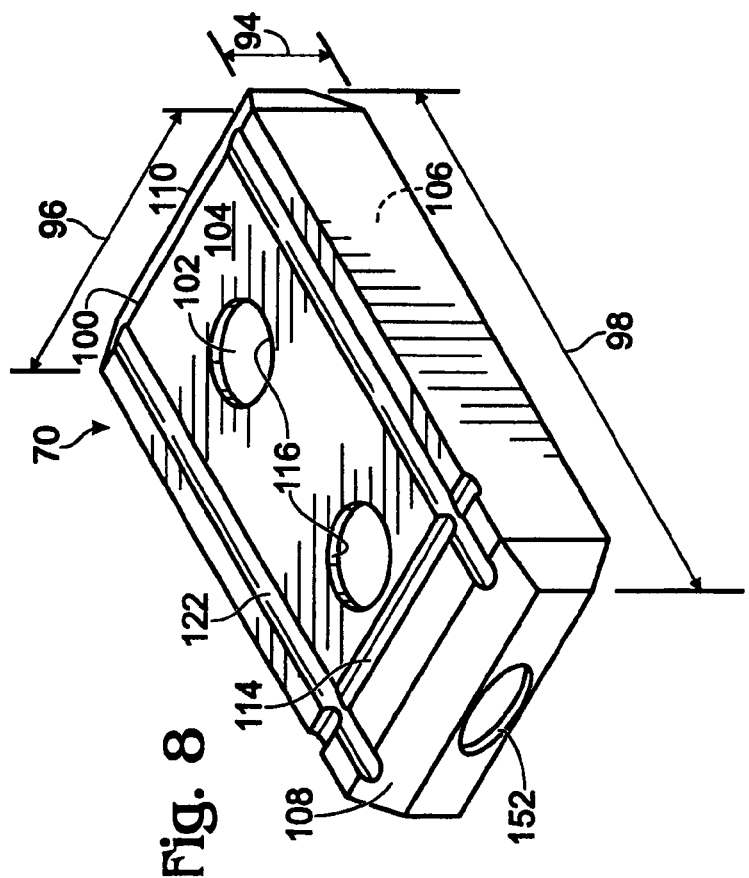
FIG. 8 is a perspective view of a material restrictor according to an embodiment of the present disclosure.

A perspective view of an exemplary embodiment of a material restrictor 70 is shown in FIG. 8. In some embodiments, the size of the material restrictor may be minimized as the material restrictor may primarily be used as a delivery device for the fusing material into the disc space and the adjacent vertebral bodies. For example, in some embodiments, the width of the cage may be decreased enabling reduced surgical exposure and nerve root retraction, similar to the exposure used for a simple micro-lumbar disectomy. This ability to reduce exposure to the disc space may speed patient recovery and reduce required hospital stays which occur with the prior fusion methods and systems. Additionally, reducing the amount of exposure may make the procedure easier and more reliable, thus improving the patient's outcome.

The height 94 of the material restrictor 70 may correspond to the normal height of the disc space in which the material restrictor is to be inserted. For example, the height of material restrictor 70 may range from about 8 mm to about 14 mm to reestablish normal height of the disc space. A practitioner may select a different height (as well as other dimensions) for the material restrictor based on a patient's needs.

The width 96 of an embodiment of a material restrictor 70 is also shown in FIG. 8. In one embodiment, material restrictor 70 may be about seven millimeters in width. Seven millimeters was chosen based on interoperative measurements made during micro lumbar discectomies. A seven-millimeter width may allow for insertion through an opening created through the small hemilaminotomy with minimal facet joint removal as described above. However, it should be appreciated that other widths may be used without departing from the scope of the present disclosure.

Material restrictors 70 of the present disclosure may be of any suitable length 98. The length 98 of material restrictor 70 may be selected based on a patient's needs. In some embodiments, material restrictors 70 may have standardized lengths that cooperate with stops 78 on delivery tangs 62, 64 to place material restrictor 70 in the desired predetermined position between vertebral bodies 80. For example, material restrictor 70 may have a length of 20 mm, while other restrictors may have a length of 26 mm. In even other embodiments, restrictor 70 may have a length ranging from about 18 mm to about 28 mm. However, other suitable lengths may be used as desired by the practitioner without departing from the scope of the present disclosure.

Additionally, in some embodiments, material restrictor 70 may be configured with straight or lordotic curves. The curvature of the material restrictor 70 may correspond to the curvature of the region of the disc in the spine. Further, the tangs may also be suitably curved to aid in placement of the delivery device and/or placement of the material restrictor.

As shown in FIG. 8, material restrictor 70 may include a shell 100 that defines a central cavity 102. Shell 100 may have a top surface 104 and a bottom surface 106 as well as ends 108, 110. In some embodiments, one end 110 of material restrictor 70 may be substantially closed and the other end 108 may be at least partially open (e.g. opening 152). Central cavity 102 and the various openings in shell 100 will be described in more detail below. It should be appreciated that material restrictor 70 may be composed of any suitable material. For example, in some embodiments material restrictor 70 may be made of titanium or a biodegradable material.

Material restrictor 70 may include structures which enable the material restrictor to controllably travel along delivery device 60. In some embodiments of material restrictor 70, such as the embodiment shown in FIG. 8, at least one of the top and bottom surfaces 104, 106 may include positioning and/or alignment features, such as channels 122. In some embodiments, the positioning and/or alignment features of the restrictor may correspond with positioning and/or alignment features of delivery device 60.

In an exemplary embodiment, material restrictor 70 may include alignment channels which correspond with projections provided on tangs 62, 64, or vice versa. For example, material restrictor 70 may include longitudinal channels 122 configured to cooperate with projections or ridges on delivery device 60 to form an alignment system. The alignment system may function to prevent material restrictor 70 from slipping sideways out of delivery tangs 62, 64, which could cause undesired injuries, such as nerve root injury.

Additionally, material restrictor 70 may be provided with one or more transverse channels (positioning features) 114 configured to cooperate with ridges or other like structure of delivery device 60 when the material restrictor reaches a select position. These positioning features 112 may provide feedback to the practitioner indicating that material restrictor 70 has reached the desired position.

The material restrictor may be configured to deliver the fusing material into the disc space and the adjacent vertebral bodies. In some embodiments, the material restrictor functions as scaffolding to maintain vertebral disc space and alignment. Structures may be provided within the material restrictor to enhance the scaffolding effect and/or to increase the rigidity of the bridge formed when the fusing material is introduced.

Material restrictor 70 may include a delivery surface. In some embodiments, the delivery surface may be considered the top and bottom of the material restrictor. The delivery surface may include one or more preformed openings or delivery holes 116. In alternative embodiments, the delivery surface may include delivery holes 116 that may be formed by drilling through the surface of the restrictor after placement of the restrictor or prior to placement of the restrictor. Delivery holes 116 may provide a channel for material to flow from the restrictor into the adjacent bone.

Material restrictor 70 may further include an injection opening 125 configured to receive fusing material into cavity 102. The injection opening may be sized to correspond to a delivery cannula. Alternatively and/or additionally, the restrictor may include structure enabling attachment of the delivery cannula such that material may be passed into cavity 102. Although shown in FIG. 8, as an oval opening, any suitable opening may be used, for example, in some embodiments, the entire end 108 may be open.

Figure 8A:
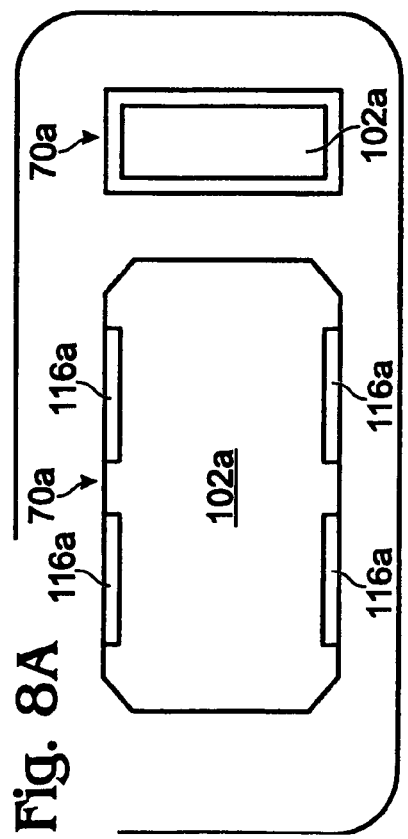
FIG. 8a is a schematic illustration of another material restrictor according to an embodiment of the present disclosure.

FIG. 8*a* further provides another schematic illustration of a material restrictor. Specifically, material restrictor 70*a* is shown with cavity 102*a* and delivery holes 116*a*. As shown, the restrictor may be hollow such that fusing material may flow through the restrictor and out through delivery holes 116*a*.

Figure 9:
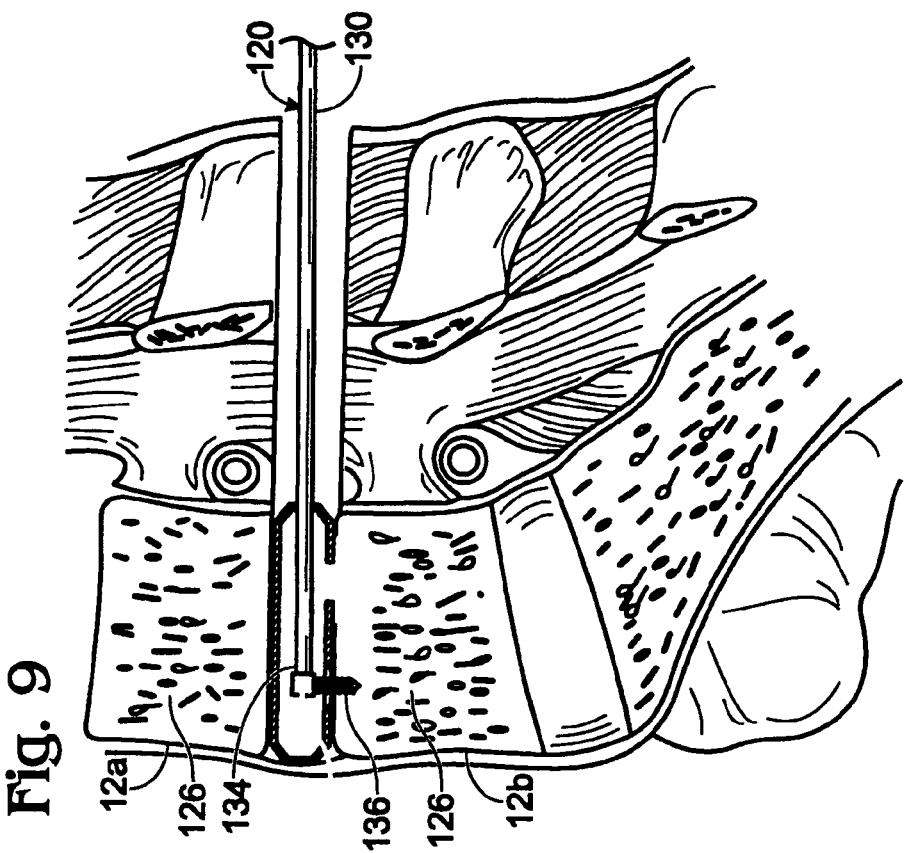
FIG. 9 is a simplified illustration of the use of a drill to create a delivery channel into a vertebral body according to an embodiment of the present disclosure.
Figure 10:
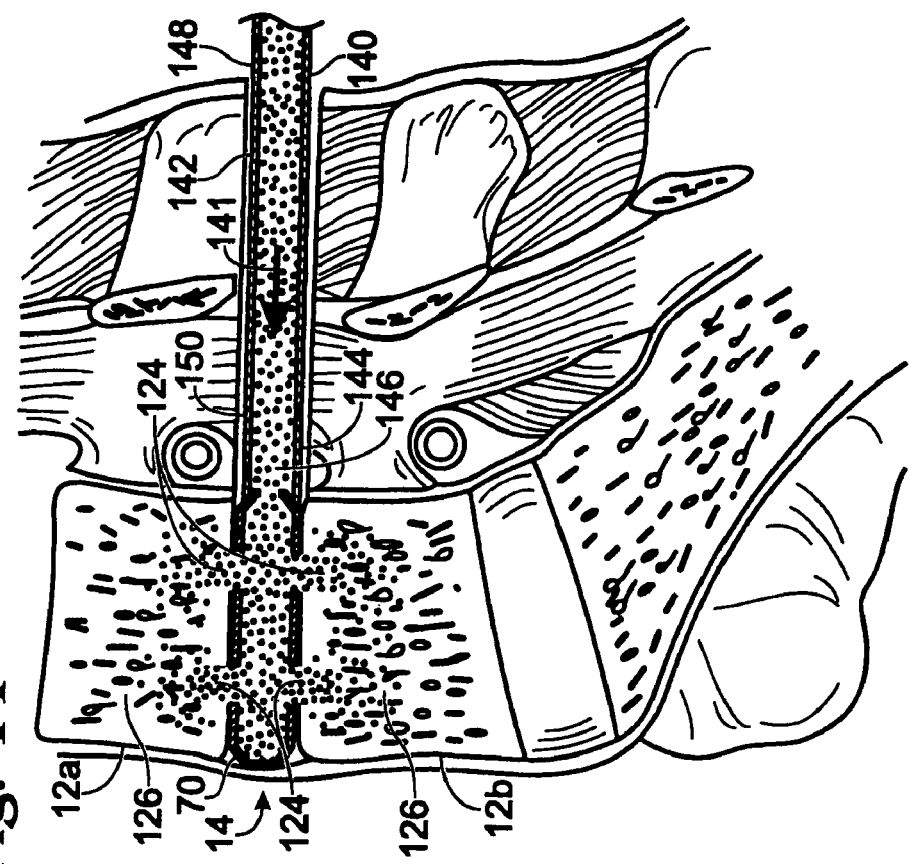
FIG. 10 is a simplified illustration of a disc space prepared for fusion according an embodiment of the present invention.

With continued reference to FIG. 3 and with reference to FIGS. 9 and 10, once the material restrictor is in a select position, delivery channels into the cancellous bone may be formed (at 50 in FIG. 3). Such delivery channels may be drilled from a central cavity of the material restrictor through delivery holes 116 (or creating delivery holes 116) into the cancellous bone of each of the adjacent vertebral bodies.

In some embodiments, such as the embodiment depicted in FIG. 9, a drill 120, such as an endplate drill or similar device, may be utilized to drill a plurality of channels. Drill 120 may be configured to break the cortical walls of the endplate to create delivery channels 124 that are adapted to allow injected material to spread within the cancellous bone 126 of vertebral bodies 12*a*, 12*b*.

Any suitable device may be used to create the delivery channels. In one embodiment, a guided locking cannula with an internal flexible drill that extends at an angle, such as approximately 90 degrees, from the long axis of the drill may be used. Drill 120 may include an elongate shaft 130 having a longitudinal axis and an insertion end 134 configured to be inserted into material restrictor 70. Drill 120 may further include a rotatable tip 136 disposed adjacent insertion end 134 of elongate shaft 130. Rotatable tip 136 may be configured to extend away from shaft 130 normal to the shaft's longitudinal axis.

It should be appreciated that the restrictor may include an opening configured to receive insertion end 134 and rotatable tip 136 of drill 120. The drill may be aligned with such openings to ensure formation of flow through channels. Alternatively, a drill may be used to form openings within the restrictor.

Although a specific drill is disclosed, other channel-making devices may be used without departing from the scope of the disclosure. Moreover, drilling may occur while the delivery device is maintained in place. However, in other embodiments, the delivery device may be removed by breaking the handle portion away from the restrictor portion. Alternatively, the tangs may be removed by gently rocking the tangs back and forth. Removal of the tangs and/or removal of a portion of the tangs may occur at any step of the method as dictated by the procedure and/or practitioner.

In some embodiments, drilling delivery channels (as indicated at 50 in FIG. 3) may include drilling through a first and a second opposing surface of the material restrictor, such as a top and a bottom surface. In other embodiments, the material restrictor may be provided with delivery holes 116, shown in FIG. 8, in one, or both, opposing top and bottom surfaces prior to insertion into the disc space. Additionally, the step of drilling delivery channels into the cancellous bone may include drilling through the cortical bone of each of the adjacent vertebral bodies.

Referring back to FIG. 9, a first delivery channel has been formed with a second delivery channel in the process of formation. In some embodiments, four delivery channels 124 may be drilled, such as shown in FIG. 10. Although four delivery channels are illustrated in FIG. 10, any number of channels may be used. For example, in some embodiments, one, two, three, four, five or more channels may be utilized. Moreover, the number of channels and the placement of channels may be selected based on several factors including the desired amount of fusing material to be delivered, the size of the vertebral bodies to be fused, and the configuration of the material restrictor used.

With continued reference to FIG. 3, once the delivery channels are prepared, a fusing material may be delivered to the material restrictor and to the adjacent vertebral bodies via the delivery channels, (indicated at 52 in FIG. 3). The configuration enables deliver of fusing material, such as biological material, via the disc space to bridge into the cancellous bone above and below the disc space. As the fusing material spreads into the cancellous bone, above and below the disc space, a strong bridge may be produced fusing the vertebral bodies together. Due to the structure of the bone, the cortical surface will restrict the fusing material to the cancellous bone. The porous structure of the cancellous bone enables the fusing material to spread and extend into the vertebral bodies, both strengthening the vertebral bodies and creating a solid bridge between the vertebral bodies.

It should be noted that in some embodiments, the material restrictor is not the device which is being used to support the bridge. Instead, in such embodiments, the material restrictor simply operates to deliver the fusing material into the disc space and the adjacent vertebral bodies such that the fusing material defines the strength of the construct. In other embodiment, structure within the material restrictor may enhance the strength of the bridge or construct, such as providing reinforcing structures within the bridge. For example, reinforcing bars or the like, may be included within (or introduced into) the material restrictor or the fusing material to increase the strength of the construct.

Figure 11:
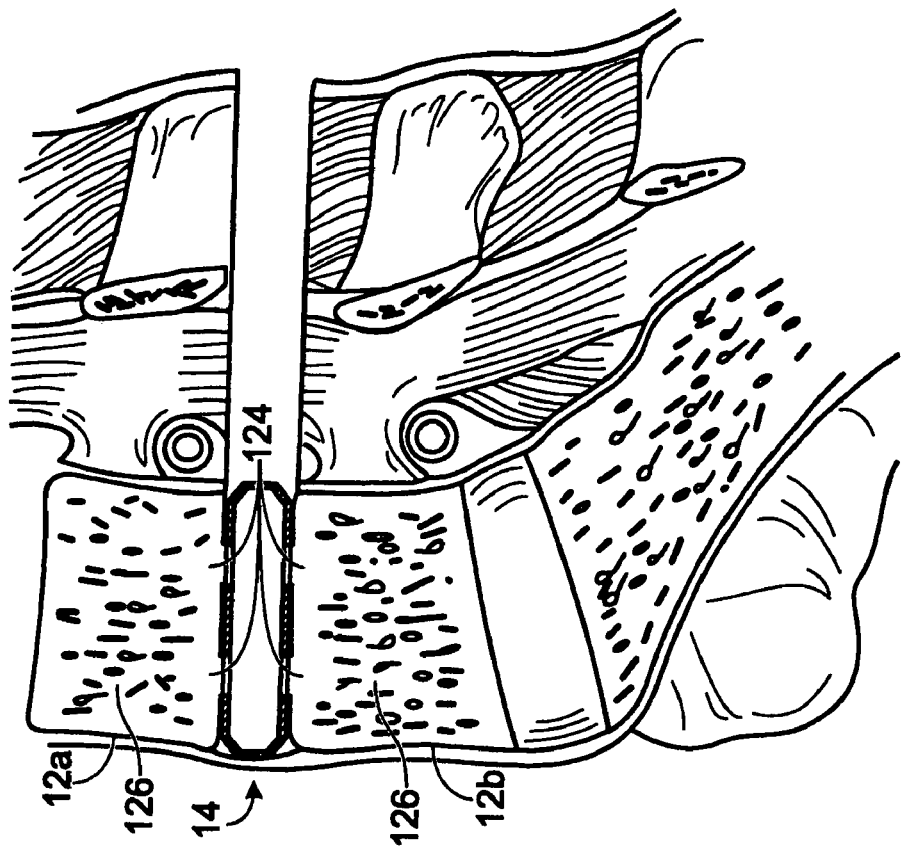
FIG. 11 is a simplified illustration of a fusing material being delivered to the vertebral bodies according to an embodiment of the present disclosure.

As shown in FIG. 11, fusing material 140 may be delivered, such as by injection, through a material delivery cannula 142, or similar device, to material restrictor 70 as indicated by arrow 141 in FIG. 11. Fusing material 140 may then pass through the delivery channels 124 into adjacent vertebral bodies 12a, 12b. Fusing material 140 may disperse through the tribecular channels of cancellous bone 126 and bridge across material restrictor 70. The fusing material may harden, cementing and securing vertebral bodies 12a and 12b with the material restrictor to create a fused vertebral section.

In some embodiments, interbody delivery device 60 may be used to deliver fusing material 140 and thus, may operate as a material delivery cannula. For example, in some embodiments, delivery device 60 may include at least two sidewalls that couple the first and second tangs along the length thereof. The sidewalls may be flexible to allow for distraction of the disc space. The sidewalls and the first and second tangs may define a lumen through which fusing material 140 may be inserted into material restrictor 70. In other embodiments, a separate material delivery cannula 142 may be coupled to material restrictor 70 and used to deliver fusing material 140. The delivery cannula may form a tight seal with the material restrictor. The delivery cannula may be coupled to the material restrictor using clamps, structural knobs, or other suitable attachment methods.

Material delivery cannula 142 may include an elongate body 144 that defines a lumen or cavity 146. The elongate body 144 includes a proximal end 148 and a distal end 150. Distal end 150 may be configured to couple with material restrictor 70 such that material may be transferred from the cannula to the restrictor. Referring to FIG. 8, coupling end of material restrictor 70 may be at least partially open to allow fusing material 140 to pass into central cavity 102. For example, the coupling end of material restrictor 70 may be provided with an injection opening 152 prior to insertion of material restrictor 70. It should be appreciated that injection opening may be of any suitable size and/or shape and may include one or more openings.

In one example, the coupling end may be partially opened by drill 120, discussed above, after material restrictor 70 is inserted into disc space 76. Material delivery cannula 142, thus, may be configured to couple with material restrictor 70 such that the opening of the material restrictor is in communication with lumen 146 of material delivery cannula 142.

Fusing material 140 may be any suitable biomaterial. In some embodiments, the fusing material may be a bioadhesive material. For example, the fusing material may be a biocompatible, bioabsorbable, osteoinductive material. In some embodiments, fusing material 140 may be a biological cement. The cement may be configured to harden into a solid after a short period of time, such as less than about 10 minutes. For example, in one embodiment, a biological cement may be used which initially flows as it is injected into material restrictor 70 and prepared vertebral bodies 12a, 12b. In some embodiments, the flowing biological cement may be configured to harden within 2–3 minutes. The hardening of the biological cement may set the construct and achieve a solid fusion.

Various materials or combinations of materials may be used as fusing material 140. Each of the following materials is provided for illustrative purposes and is not intended to limit the scope of the disclosure. For example, in some embodiments, Simplex or similar material may be used as a rigid stand-alone fixation. As the biological cement spreads through the cancellous bone, across the material restrictor, into the opposite vertebral body, forming a rigid fixation, the material strength and durability may become the rate-limiting factor. Another option may be the use of Simplex or similar material with allograft and bone morphogenetic protein over the facet joints, thus developing a solid bony fusion.

The fusing material may be a bioadhesive material that provides rapid hardening and substantially immediate fusion of the vertebral bodies. In some embodiments, the fusing material may have a short curing period, reduced exothermic behavior during polymerization and other mechanical properties such that the fusion remains stable over time. One exemplary fusing material and related properties may include the use of a copolymer of methyl-methacrylate (MMA) and diethyl-amino-ethyl methacrylate (DAEMA) which may provide controlled curing temperature and good mechanical properties. Inclusion of hydroxyapatite may improve bone-fusing material interaction. Further, a dispersion of polylactide (PLA) may be used to create a segregated phase, with bioresorbable properties.

In yet another embodiment, a bone substitute material may be injected through the material restrictor that will form a substantially immediate rigid fixation. The bone substitute material may carry BMPs and may be adapted to be reabsorbed and replaced with bone over time. For example, the fusing material may be configured to be biodegraded while osteoinductive properties simulate bone grown for physiologic fusion of the vertebral bodies. In one embodiment, the fusing material may be configured to substantially immediately form the stabilized bridge for a period of 6 to 12 months as the bone growth occurs.

It should be noted that in some embodiments, other types of delivery structure may be used to deliver the fusing material into the disc space and the adjacent vertebral bodies. For example, in some embodiments, pedicles adjacent to the disc space may be used to introduce fusing material into the disc space and the vertebral bodies.

Figure 12:
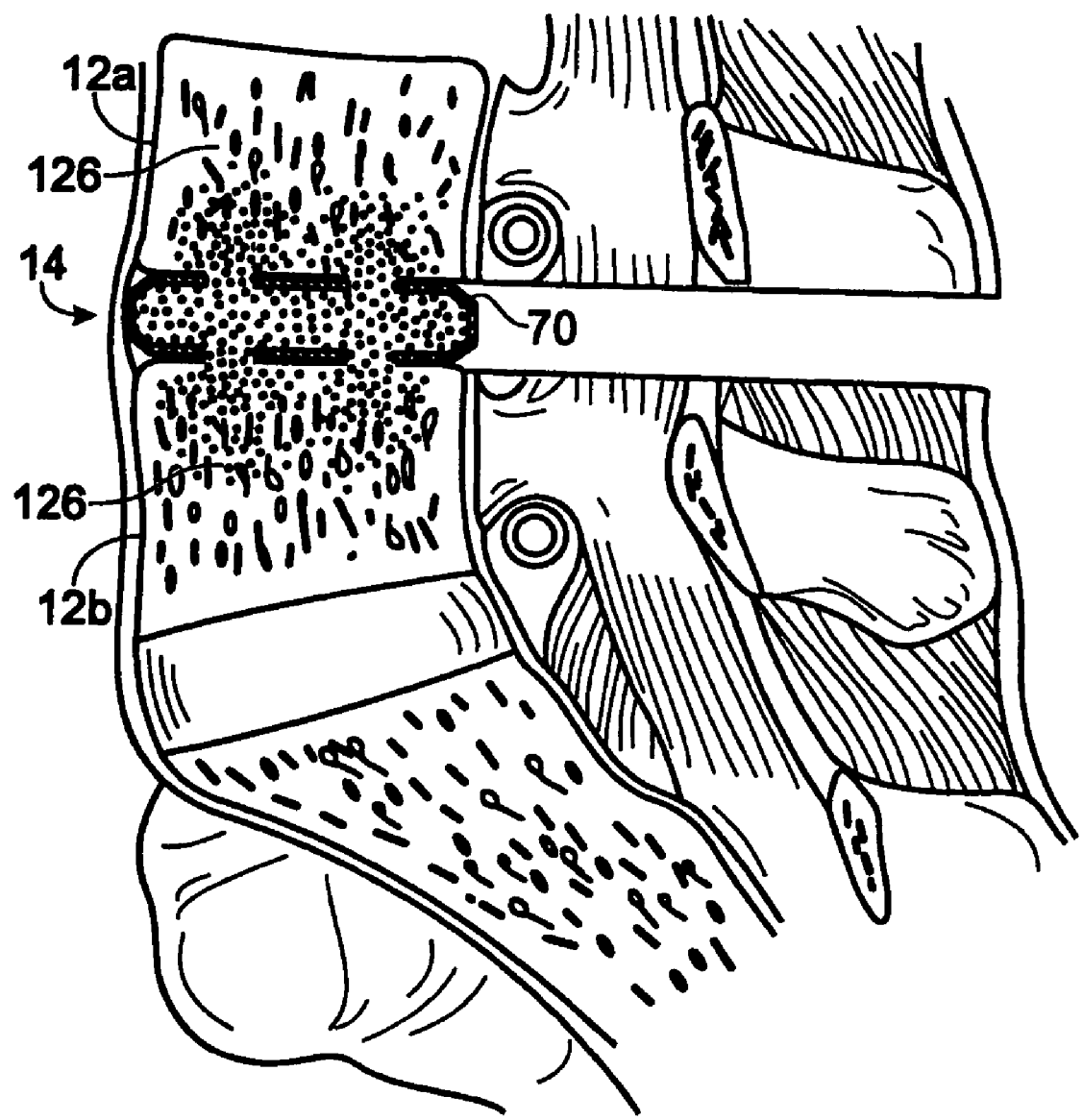
FIG. 12 is a simplified illustration of a completed AMLIF with fusing material extending between the vertebral bodies and a material restrictor according to an embodiment of the present disclosure.

FIG. 12 illustrates an intervertebral disc space 14 after one embodiment of the augmented micro lumbar interbody fusion method of the present disclosure is completed. Material restrictor 70 is positioned intermediate the adjacent vertebral bodies 12a, 12b. Fusing material 140 fills material restrictor 70 and has spread into cancellous bone 126 of each of the adjacent vertebral bodies 12a, 12b. Fusing material 140 stabilizes vertebral bodies 12a, 12b; anchors material restrictor 70 in place, and enables for development of a rigid osseous construct in intervertebral disc space 14.

Figure 13:
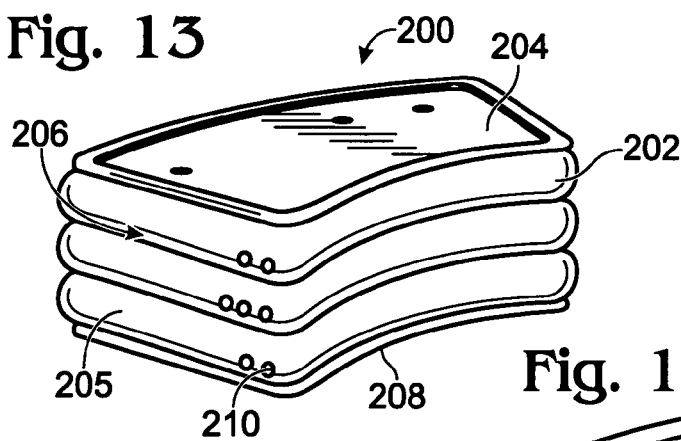
FIGS. 13 and 13a are schematic illustrations of another embodiment of a material restrictor according to an embodiment of the present disclosure.
Figure 13B:
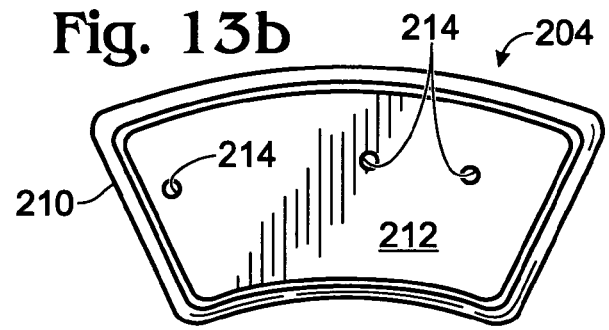

FIGS. 13–20 further illustrate additional embodiments for the above methods, systems and apparatus. It should be appreciated that the description and illustration of these embodiments are for illustrative purposes and are not intended to be limiting in any fashion. For example, FIG. 13 provides an alternative embodiment of a material restrictor 200. Material restrictor 200 is shown as a kidney-shaped cage, however other suitable shapes are considered and are within the scope of this disclosure. In some embodiments, material restrictor 200 may include sidewalls 202, 205. The sidewalls may be flexible, expandable walls (indicated at 206) enabling the restrictor to distend into a trapezoidal shape upon introduction of fusing material. Thus, in some embodiments, restrictor 200 may be expandable. However, in other embodiments, restrictor 200 may be a static configuration. In one or more sidewalls, inlet ports or injection opening, 210 may be provided.

Restrictor 200 may further include a top surface 204 and a bottom surface 208. Top surface 204 and bottom surface 208 may be configured to contact the endplate of the vertebral bodies and prevent subsidence into the bodies. In some embodiments, the top and bottom surfaces may be made of a substantially rigid material.

FIG. 13a further illustrates a top view of top surface 204. Bottom surface 208 may be similarly constructed to top surface 204. As shown, top surface 204 may include a plurality of delivery holes, such as fusing material release points or outlet ports 214. These outlet ports may be subsequently drilled after placement of the restrictor within the disc space. Surface 204 may further include a seal 212, such as a gasket perimeter seal, to ensure a tight closure between the restrictor and the vertebral bodies.

Figure 14:
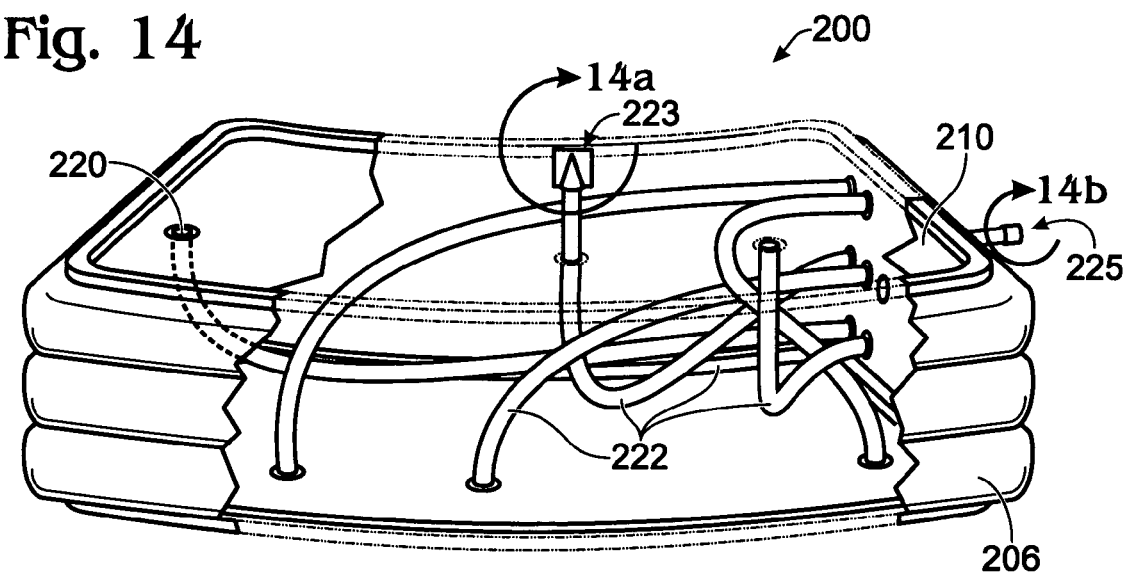
FIGS. 14, 14a and 14b are additional illustrations of a material restrictor including distribution channels according to an embodiment of the present disclosure.

FIG. 14 further illustrates restrictor 200. As shown in FIG. 14, in some embodiments, restrictor 200 may include one or more distribution channels 220, 222. The distribution channels may connect from a side wall with inlet ports 210 to outlet ports 214 disposed in the top and bottom surfaces 204, 208.

Figure 14A:
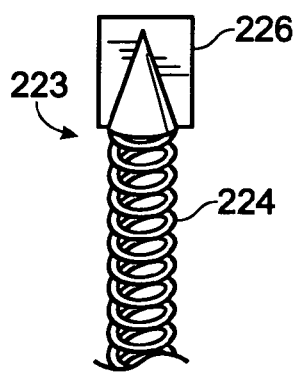
Figure 14B:
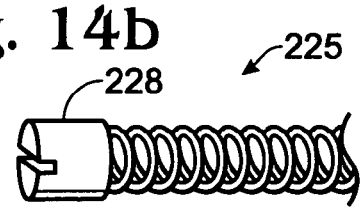

FIGS. 14a and 14b further illustrate an exemplary distribution channel 222. Referring back to FIG. 14, for purposes of understanding FIG. 14, a first end of a distribution channel is indicated at 223 and a second end of a distribution channel is indicated at 225. FIG. 14a provides an enlarged view of first end 223 of the distribution channel. As shown, first end 223 includes a compressed drilling spring ending with a drill bit 228. Drill bit 228 may be configured to penetrate the vertebral cortical endplate bone and cavitate or drill into the softer cancellous bone of the vertebral bodies. By drilling into the cancellous bone, a larger receptacle zone may be provided for the fusing material.

FIG. 14b illustrates an enlarged view of second end 225 of a distribution channel, including compressed drilling spring 224 and a terminating end, with a socket 226. The distribution channel may enable precise drilling into the inner cortical surface of the vertebral bodies. For example, a device may be linked to socket 226, thus effecting drill bit 228 to penetrate into the vertebral bodies. In some embodiments, this drilling spring (distribution channel) may be configured to remain with the vertebral body such that the distribution channel operates as a strengthening or reinforcing structure to the fusing material. Further by leaving the distribution channel, it may be possible to enhance the tensile and shearing force resistance at the cage-endplate interface. In other embodiments, the distribution channel (such as the spring-drill or drilling spring) may be removed or otherwise positioned within the restrictor or the space.

FIG. 15 illustrates an embodiment for a delivery device 250. Delivery device 250 may be configured to deliver restrictor 200 into the exposed disc space. As shown, delivery device 250 may include a handle 252 and an extension portion 254. Terminating at the end of extension portion 254 is an insertion end 258 of delivery device 250. Insertion end 258 may include rails or tangs 256 for insertion of restrictor 200.

FIG. 15a further illustrates insertion end 258 of exemplary delivery device 250. As illustrated, insertion end 258 may be shaped to aid in directing and insertion of the restrictor into the disc space. For example, tangs 256 may be shaped or curved, such as c-shaped, to aid in placement of restrictor 200 within the space. As described above, tangs 256 may have alignment features to guide restrictor 200 into a desired location.

Delivery device 250 may include a guiding structure, such as a plunger 260, adapted to release restrictor 200 into the,select position in the disc space. In some embodiments, plunger 260 may be operable from the handle of the device.

FIG. 16 further illustrates operation and features of an exemplary delivery device 250. Specifically, in the exemplary embodiment, delivery device includes alignment features which correspond to alignment features on the restrictor. For example, delivery device 250 may include a plunger 260 with guide tubes 262. These guide tubes 262 may correspond to inlet ports 210 on restrictor 200. Guide tubes 262 may be coupled to sockets 262 of drilling springs 224 and a tube that is connected to the injection or inlet port 210 used to fill restrictor 200 with the fusing material. Thus, the delivery device may be operatively coupled to the material restrictor.

FIG. 16a further illustrates another end 253 of delivery device 250. Although shown as being on the end of delivery device 250, such features may be provided on any suitable surface or side of deliver device 250. Specifically, as illustrated, one or more connection ports 264, 266 may be provided which may enable a DREMEL® or other suitable tool to be coupled with delivery device 250 to operate spring drills contained within restrictor 200. In some embodiments, these same ports, or like ports, may be coupled to a tube or be configured to receive a tube to deliver fusing material to restrictor 200. A map or other indicator surface, such as shown at 265, may also be provided to aid a user in selectively drilling or connecting to structures within restrictor 200.

Figure 17A:
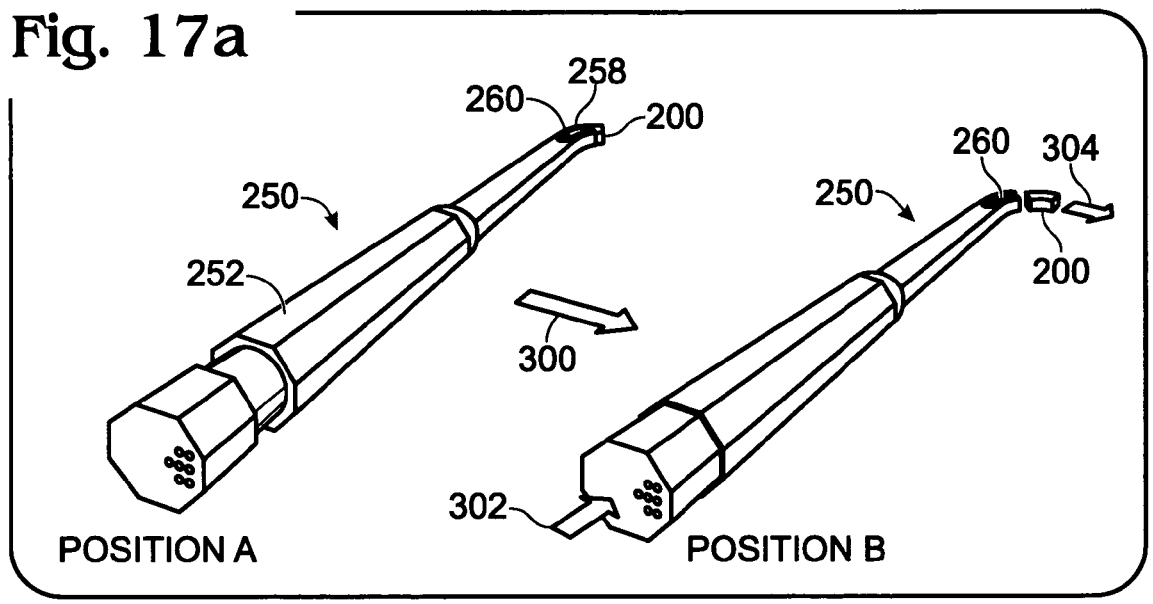
FIG. 17a illustrates a first operation of a delivery device for insertion of a restrictor into a disc space according to an embodiment of the present disclosure.

FIG. 17a–20 illustrate a method of AMLIF. It should be appreciated that although described with use of restrictor 200, and delivery device 250, other types of restrictors and delivery devices, as described herein may be used and such illustrations are not intended to be limiting. In FIG. 17a, at Position A, a delivery device 250 is shown having a handle 252 and an insertion end 258. An enlarged view of insertion end 258 is shown in Position B. As shown in Position B, a restrictor 200 may be positioned within tangs 256 of delivery device 250.

Arrow 300 indicates transition of delivery device 250 from position A to Position B. Specifically, as indicated by arrows 302, 304 (and shown in FIGS. 17a and 17b at Position B), plunger 260 may be moved such that restrictor 200 is pushed into place by delivery device 250. Although shown as being fully removed from the delivery device, such discharge of the restrictor is shown for illustrative purposes and it should be appreciated that any suitable configuration may be used for placement of the restrictor. For example, in some embodiments, select positions may be used to position the restrictor, such that release from the delivery device is delayed by using intermediary release positions. Further, as discussed above, portions of the delivery device may be configured to breakaway from the delivery device remaining with the restrictor in the space. Thus, in use, a surgeon may selectively position delivery device 250 and position restrictor 200 into a disc space by moving plunger 260. Any suitable method may be used to move plunger 260. For example, in some embodiments, pushing the bottom of the handle or other suitable lever may result in motion of plunger 260.

Figure 18A:
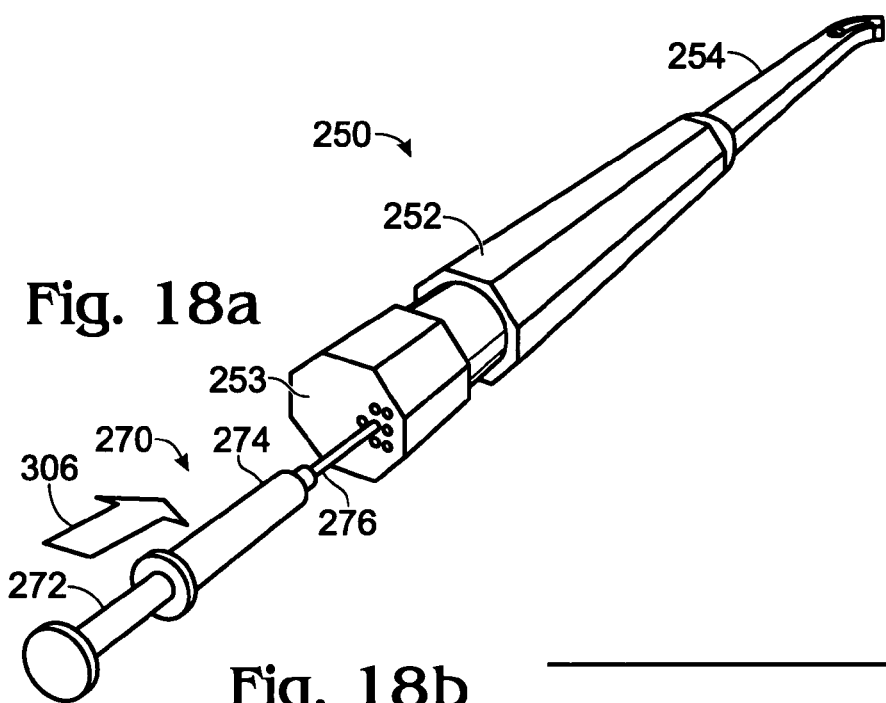
FIGS. 18a and 18b illustrate insertion of fusing material through a delivery device into a restrictor according to an embodiment of the present disclosure.
Figure 18B:
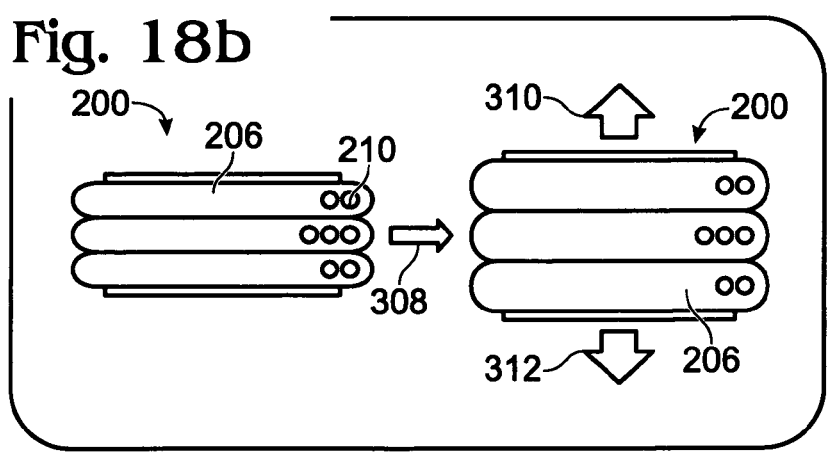

FIGS. 18a and 18b illustrate one exemplary method of filling restrictor 200 with fusing material. As shown, fusing material may be stored or disposed in a syringe 270 or other suitable device. Syringe 270 may include a body 274 and a user-manipulable portion 272 to control release of the fusing material. Syringe 270 may be positioned such that the syringe tip 276 engages one of the connection ports, such as 266, of delivery device 250. In some embodiments, a main valve may be provided which enables direct release of fusing material into the central cavity of the restrictor. Thus, a user inserts (indicated at 306) fusing material from syringe 270 into delivery device 250 through to restrictor 200. FIG. 18b illustrates the expansion of restrictor 200, such that as fusing material fills restrictor 200 (indicated by arrow 298), restrictor 200 expands outward as indicated by arrows 310, 312.

Prior to or after filling of the restrictor (main cavity) with fusing material, delivery channels' may be created into the vertebral bodies. FIG. 19*a* shows attachment of a DREMEL® or other drilling device 280 to delivery device 250. Drilling device 280 may include a body 282 and a drill 284. Drill 284 may be configured to operatively engage socket 226 of compressed drilling spring 224 within restrictor 200 (see FIG. 14*a* and 14*b*). Drill 284 may operatively engage socket 226 through delivery device 250, such as through connection port 266. Arrow 314 indicates insertion of drilling device 280 onto delivery device 250, while arrow 316 indicates rotation of drill 284.

FIG. 19*b* illustrates the effect of drilling device 280 on restrictor 200. Specifically, drilling device operatively, engages against socket 226 of compressed drilling spring 224 through inlet port 210. Rotation of socket 226 (indicated at 318) by drill bit 284, results in drilling spring engaging and drilling up through outlet port 214 through the cortical wall and into the cancellous bone of the adjacent vertebral body (not shown in FIG. 19*b*). Similar, drilling may take place with each distribution channel, such that a delivery channel is formed into the cancellous bone adjacent the outlet ports. Arrow 320 indicates the drilling of the cancellous bone by the end of drilling spring 223.

FIG. 20 provides a schematic illustration of the steps to insert fusing material into the cancellous bone of the adjacent vertebral bodies. It is noted that in some embodiments, the main cavity of the restrictor may be filled concurrently with, or substantially concurrently with injecting fusing material into the adjacent vertebral bodies. As described previous, a syringe 270 with fusing material may be disposed to inject fusing material into restrictor 200. For example, syringe 270 may operatively engage delivery device 250, e.g. syringe tip 276 may be selectively disposed in connection port 266 of delivery device 250. Such engagement is schematically illustrated by arrow 330.

The fusing material may flow from syringe 270 along the drilling path into restrictor 200 and out through outlet port 214 and into the prepared delivery channels of the vertebral bodies. Arrow 334 indicates the flow of fusing material into the inlet port 210 of the restrictor 200. The fusing materials flows through the channels and along the drilling springs inserted in the vertebral bodies. The material may spread through the adjacent cancellous bone, as indicated schematically at 280. The drilling springs (and related components, such as the drill bit) may be retained in position (extending out from the restrictor) and may function as reinforcement structure thus increasing the strength of the fusion.

As described above, the fusing material may rapidly harden, thus fusing the vertebral bodies together. Arrow 336 schematically illustrates the restrictor 200 as disposed in the disc space with the fusing material extending from each of the outlet ports into the vertebral bodies indicated at 280. Since the fusing material rapidly hardens, the vertebral bodies will be quickly stabilized. Such a procedure may be simple enough and provide a strong enough fusion of the vertebral bodies for a patient to be able to be treated using same day surgery, outpatient surgery or minimal hospital stays. Further the recovery period and costs associated with the procedure may be significantly decreased.

It should be appreciated that the above methods, systems and apparatus substantially reduce the recovery periods currently required using prior fusion methods. In prior methods, an interbody cage was tightly wedged into the disc space. Bone was then packed into the cage with the potential to grow through the cage walls over time fusing the vertebral body above and below. Substantial time was required for the bone to harden, thus affecting a patient's recovery time. If the cage were to loosen before bone growth could take place, a pseudoarthrosis or nonunion occurred.

In contrast, the material restrictor and method described herein is configured to deliver fusing material which is configured to harden rapidly, thus substantially immediately forming a stabilized construct. Thus, substantially minimizing the chances of pseudoarthrosis or nonunion. Further, since the material restrictor functions as a delivery device for the fusing material, the size of the delivery device may be minimized such that less of the disc space needs to be exposed. The reduced exposure and substantially immediate formation of the construct improve recovery periods and reduce hospital stays. For example, it may be possible to perform the above method on an out-patient basis. The simplified technique may further improve the safety levels for the surgical treatment. By reducing recovery periods, decreasing hospital stays, and increasing safety levels, costs for the procedures may be reduced and the patient outcome may be improved.

Generally, and as described above, the disclosed methods, systems and apparatus provide for a minimally-invasive procedure for fusing one or more vertebral bodies together. The narrowness of the material restrictor enables the use of small incisions with minimal disruption of the spinal anatomy. Due to the minimally invasive nature of the procedure, hospital stays should be no longer than for a simple micro lumbar discectomy. The injected fusing material not only fuses the vertebral bodies together but also further restricts subsidence and migration of the cage. Patients with osteoporosis and similar conditions may also be treated because the cement injection essentially functions as a vertebroplasty. The disclosure set forth above encompasses multiple distinct inventions with independent utility. Although the present disclosure includes specific embodiments, specific embodiments are not to be considered in a limiting sense, because numerous variations are possible. The subject matter of the present disclosure includes all novel and nonobvious combinations and subcombinations of the various elements, features, functions, and/or properties disclosed herein. The following claims particularly point out certain combinations and subcombinations regarded as novel and nonobvious. These claims may refer to "an" element or "a first" element or the equivalent thereof. Such claims should be understood to include incorporation of one or more such elements, neither requiring, nor excluding two or more such elements. Other combinations and subcombinations of features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

What is claimed is:

1. A method for interbody fusion of adjacent vertebral bodies, the method comprising:

inserting a delivery device into a disc space;

inserting a material restrictor in a disc space including guiding the material restrictor along a portion of the delivery device to a select position in the disc space;

preparing the vertebral bodies for fusion, including drilling at least one channel from a central cavity of the material restrictor into at least one of the adjacent vertebral bodies; and delivering fusing material to the material restrictor such that the fusing material extends into the adjacent vertebral bodies.

2. The method of claim 1, wherein inserting the delivery device includes retracting neural material.

3. The method of claim 1, wherein the delivery device is provided with at least one stop configured to rest against at least one of the adjacent vertebral bodies when the delivery device is fully inserted.

4. The method of claim 1, wherein guiding the material restrictor includes enabling operative connection between the material restrictor and the delivery device.

5. The method of claim 1, wherein guiding the material restrictor includes operation of guiding and/or alignment structures on at least one of the delivery device and the material restrictor.

6. A method for interbody fusion of adjacent vertebral bodies, the method comprising:

inserting a delivery device into a disc space;

inserting a material restrictor in a disc space including guiding the material restrictor along a portion of the delivery device to a select position in the disc space;

preparing the vertebral bodies for fusion, wherein preparing the vertebral bodies includes drilling through at least one of a top and a bottom surface of the material restrictor; and delivering fusing material to the material restrictor such that the fusing material extends into the adjacent vertebral bodies.

7. The method of claim 6, wherein inserting the delivery device includes retracting neural material.

8. The method of claim 6, wherein the delivery device is provided with at least one stop configured to rest against at least one of the adjacent vertebral bodies when the delivery device is fully inserted.

9. The method of claim 6, wherein guiding the material restrictor includes enabling operative connection between the material restrictor and the delivery device.

10. The method of claim 6, wherein guiding the material restrictor includes operation of guiding and/or alignment structures on at least one of the delivery device and the material restrictor.

11. The method of claim 6, where preparing the vertebral bodies for fusion includes drilling at least a channel into at least one of the adjacent vertebral bodies.

* * * * *